United States Patent [19]

Meckler

[11] 4,183,355
[45] Jan. 15, 1980

[54] EYE MEDICATION DISPENSING FRAMES

[76] Inventor: Milton Meckler, 16348 Tupper St., Sepulveda, Calif. 91343

[21] Appl. No.: 874,409

[22] Filed: Feb. 2, 1978

[51] Int. Cl.$^2$ .............................................. A61M 1/00
[52] U.S. Cl. .................................... 128/233; 128/249
[58] Field of Search ................. 128/233, 249, 260; 351/41, 45, 158

[56] References Cited

U.S. PATENT DOCUMENTS

| 2,600,920 | 6/1952 | Raschkind | 128/249 |
| 3,446,209 | 5/1969 | Macha | 128/233 |

FOREIGN PATENT DOCUMENTS 190022 12/1922 United Kingdom ................. 128/249

Primary Examiner—John D. Yasko
Attorney, Agent, or Firm—William H. Maxwell

[57] ABSTRACT

A frame for therapeutic self-administration of medication to the eyes and comprised of transparent right angularly related slides with normal slots therethrough for the reception of guide-adjustment-lock means, for the selective positioning of said slides, for locking the same positioned, and for receiving the medication dropper stopped in alignment with a target area of the eye.

13 Claims, 6 Drawing Figures

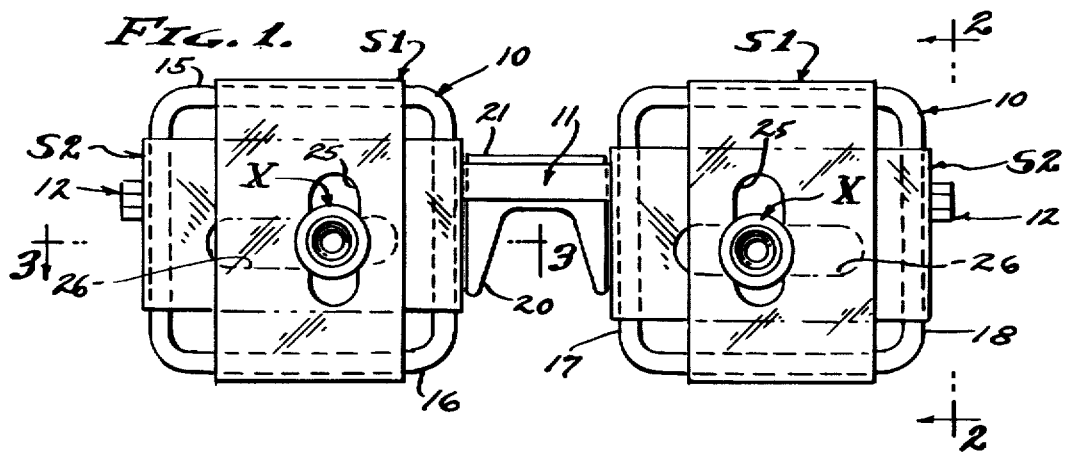
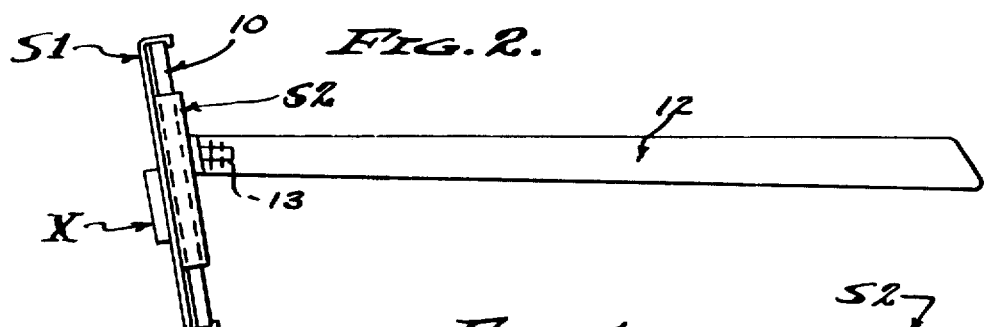
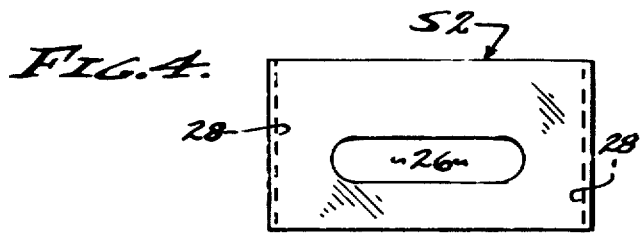
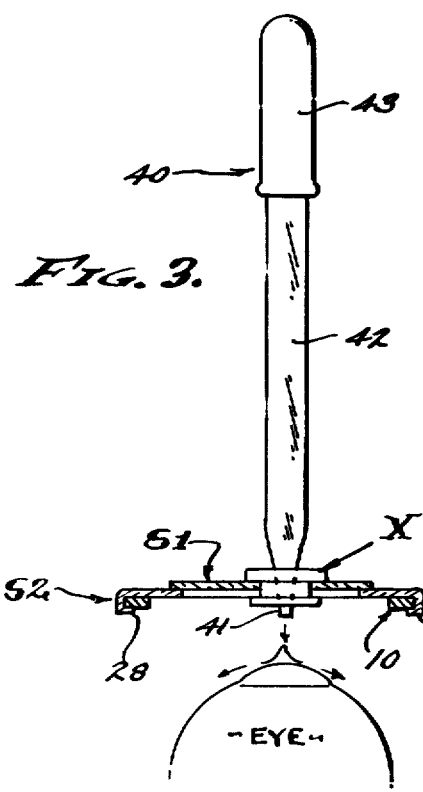
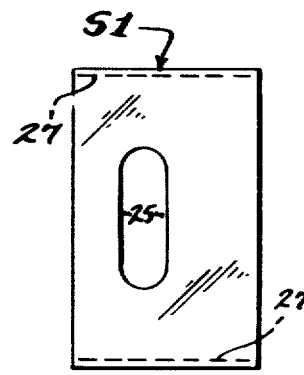
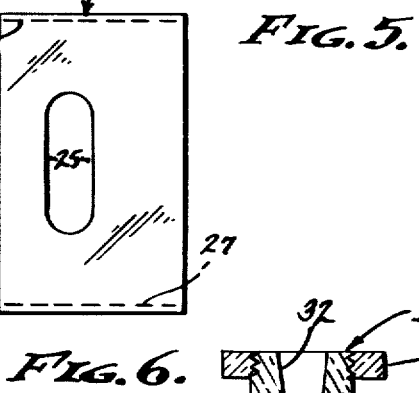
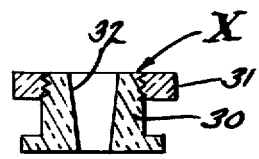

4,183,355

EYE MEDICATION DISPENSING FRAMES

BACKGROUND

The human eye is the organ of sight or vision, a substantially durable globe or ball that is moveable in the orbit or socket. Protection for the eye is provided for in the lids and lashes, and which are very sensitive and subject to involuntary or reflex action when the eye is disturbed by the approach or touching of foreign objects. Consequently the administering of medication to the eye can be difficult, and especially for those who are muscularly afflicted, simply aged, or in any way incapacitated in a manner to affect dexterity and/or equilibrium. Generally it is difficult for any person to administer medication to his own eyes, and particularly those persons who are incapacitated in a manner to adversely affect dexterity. Furthermore, the juxtapositioning of any object very close to the eye creates a condition wherein the person so administering said object cannot accurately judge position, and as a consequence the administering of liquid medication is often misdirected and thereby wasted as by washing away over the person's face. It is the use of eye-droppers for the application of medication with which this invention is concerned, namely any liquid medication that might be prescribed by an Oculist for the treatment of eye abnormalities and disease. It is, therefore, a general object of this invention to provide a therapeutic frame for self-administration of medication to the eyes, as may be prescribed by an Oculist. Although trained technicians can make the adjustments to the Oculists' prescription, it is a primary object herein for the individual person to fix the positioning of liquid application to suit the separate eyes. Further, this properly adjusted frame is adapted to be tamperproof and cannot later be maladjusted by those who are inexperienced in the anatomy of the eye. However, it is also feasible to retain adjustability of this frame for trial and/or later re-adjustment as circumstances require.

The usual optical frames are provided for mounting a pair of lenses before the eyes respectively. These frames are comprised of a bridge positioned over the person's nose, and a pair of laterally spaced rims supported by the bridge and held positioned to the person's brow by means of temples that extend therefrom to embrace the person's head over the ears. It is a frame such as this which is employed herein in combination with planar positioning means for the prescribed placement of an applicator guide to apply medication to the eye. For example, in the treatment of glaucoma, characterized by increased tension within and hardening of the eyeball, liquid medication is applied to the cornea as directly as possible; and not by indirection as might occur by flooding the eye from the corners thereof, for example. Therefore, it is an object of this invention to provide positioning means by which a prescribed placement of medication can be made according to an individual's anatomy. For instance, the inter-pupillary distance varies from person to person, and so does the height thereof with respect to the facial features; and there is of course asymmetry to be contended with. In other words, fine adjustments are to be made. Therefore, it is an object of this invention to provide for both inter-pupillary and height positioning of the aforesaid positioning means.

The transmission of light to the eye is a normal condition therefor, in order for a person to observe what is before him; darkness being detrimental. Therefore it is an object herein to provide for the transmission of light to the sensitive membranes of the eye, both for normal control of the iris and for vision, even though obstructed by the positioning means centered, for example, with the pupil in each instance. Accordingly, those members of this device which are disposed before the eyes are made of transparent material, all of which is conducive to cleanliness since smears are thereby easily detected and removed.

Inter-pupillary and height adjustment of the guide hereinabove referred to is to be retained, it being an object of this invention to provide lock means therefor. In carrying out this invention there is an individual slide for lateral and vertical adjustment and through which a clamp is engaged in right angularly related slots. As stated above, the slides are transparent members, adjustably secured by the lock means and adapted to be permanently secured by the application of solvent when required.

It is an object of this invention to cooperatively combine the aforesaid guide means, positioning means and lock means into one simple device; the lock means being a tubular clamp adapted to receive the dispensing tip of an eye-dropper and operable in said slide slots to permit adjustment. With the position determined by adjustment, the clamp means is operated to secure the slides. When absolute fixation is a requirement, solvent is applied between the (plastic) slides to fuse the same together in position.

It is also an object of this invention to provide an inexpensive and yet practical device for the proper positioning of an eye dropper for the dispensing of medicaments to the eye, directly therefrom. In other words, the medication is dispensed directly from the dropper which can be sterilized, without contamination from this therapeutic frame and positioning means which may be contaminated to some extent by handling in the process of making ready for the application of said medication.

DRAWINGS

The various objects and features of this invention will be fully understood from the following detailed description of the typical preferred form and application thereof, throughout which description reference is made to the accompanying drawings, in which:

FIG. 1 is a front elevation showing the frame of the present invention.

FIG. 2 is a side elevation taken as indicated by line 2—2 of FIG. 1.

FIG. 3 is a sectional view of one side of the frame taken as indicated by line 3—3 on FIG. 1, showing the alignment of a medication dropper with the eye.

FIGS. 4 and 5 are views of the slides taken separately and removed from the frame. And, FIG. 6 is an enlarged detailed sectional view of the guide-adjustment-lock means which characterizes this invention.

PREFERRED EMBODIMENT

It is a sensitive organ, the eye, with which this invention is concerned, providing a therapeutic frame for the Oculist to prescribe a positioning determined for the gravitational application of medication, for example directly onto the cornea. The eyeball is comprised of the segments of two dissimilar spheres. The segment of the lesser sphere forms the anterior part of the eye and is composed of a strong horn-like membrane, the cornea, within which are the aqueous humor and the iris capable of contraction and dilation with an opening, the pupil, normally centered for the transmission of light. The segment of the larger sphere forms the posterior part of the eye, and is composed of three layers, the sclerotic continuing from the cornea, the choroid continuing from the iris, and the retina which consists of a cup-like extension of the optical nerve. It is the former lesser sphere, the cornea, with which this invention is particularly concerned and for which the frame of the present invention is provided to serve in the care and healing of the eyes through the most advantageous application of medication as determined by medical science for the treatment thereof.

Referring now to the drawings, the frame of the present invention resembles a pair of eye glasses, lacking lenses and in place thereof provides transparent adjustment slides S1 and S2 and the combined guide-adjustment-lock means X for the selective positioning and fixation of the guide means thereof which locates an eye dropper received thereby. The frame can be fabricated of any suitable material, preferably plastic, and is comprised of a pair of rims 10 joined by a bridge 11, and a pair of temples 12 extending rearwardly from the hinges 13 at each rim. The rims are generally rectangular, having upper and lower rails 15 and 16 that are parallel and thereby form tracks for the horizontal slide S1, and having inner and outer rails 17 and 18 that are parallel and thereby form tracks for the vertical slide S2. The bridge 11 is a horizontal member that rigidly joins the two rims 10 in laterally spaced relation and to receive a nose piece 20. The bridge 11 is offset rearwardly from the inner rails 17 to permit movement of the slide S2. In practice, the nose piece 20 is selective for adaptation to the person's nose and has a channeled header 21 that embraces the bridge 11 and secured thereto as by means of solvent; the bridge and nose pieces being made of compatible plastic. The hinges 13 are integral with the rims, at opposite sides of the frame, being offset rearwardly thereof to permit movement of the slides S2 that hook over the rails 17-18, as will be described. The hinges extend rearwardly and outwardly from the outer rails 18, as shown. The temples 12 are bows that pivot from the hinges in the usual manner to embrace the head.

In accordance with this invention, I provide the slides S1 and S2 for the horizontal and vertical placement of the guide-adjustment-lock means X. The slides S1 and S2 are planar elements of transparent material that are interfacially engaged, one slideably over the other and each characterized by a transverse slot 25 and 26 normal to runners 27 and 28 respectively. In practice, the transparency of the slides is reduced by darkening thereof, in order to exclude excessive light and thereby reduce the tendency of squinting. The runners 27 and 28 are hook-shaped channels, opposed and engageable over the rails of the rims 10, the runners 27 of slide S1 being engaged over rails 15 and 16 while runners 28 of slide S2 are engaged over rails 17 and 18. The said runners are free to slide on the said rails, through direct manipulation thereof into the placement required, whereby the right angularly related slots 25 and 26 thereof intersect to position the means X extending therethrough.

The guide-adjustment-lock means X is comprised of a tubular barrel 30 slideably engaged through the slots 25 and 26, and a nut 31 threadedly engaged thereon. The barrel and nut are also made of transparent material, so as to be translucent, and formed so as to receive and to pass the eye dropper 40 coaxially centered therethrough. In practice, the tip 41 of an eye dropper is tapered and of a nominally small diameter, extended from a nominally large diameter body 42. The barrel carries a depressible bulb 43 at its remote end in order to provide suction for loading and pressure for dispensing medication in measured drops; all of which is customary. Accordingly, the barrel 30 has a funnel-shaped and tapered bore 32 opening toward the eye, to freely pass the tip 41 and to stop the same and the body 42 of the eye dropper; so that medication is direct from the eye dropper and so that the tip 41 is prevented from touching the eye per se (see FIG. 3). The barrel 30 is positioned by a flange fitted against the innermost slide, the nut 31 being threaded onto the barrel to seat against the outermost side. Thus, the nut 31 is accessible for manual operation when the proper position is determined.

From the foregoing, it will be seen that this therapeutic device can be easily manufactured, preferably of injection molded plastic, assembled by pinning the temples 12 to the rims 10 and by slipping the slides S1 and S2 over the parallel rim rails 15-16 and 17-18, after which the guide-adjustment-lock means X are passed through the slots 25-26 in each instance. Remaining loose, the means X permits selective shifting of the slides S1 and S2. And, a nose piece 20 is selected and pressed onto the bridge 11. The frame assembled as thus far described is then fitted to the person or by the person who is thereafter to administer medication to their own eye or eyes by means of an eye dropper 40 inserted through the bores 32 of means X. The frame is fitted to the head and features of the person, followed by selective positioning of the slides S1 and S2 dependent upon the posture to be taken by the person who is to administer his drops of medication, it being recognized, for example, that there will be a different alignment required for a person merely tilting his head back as compared with a person who will be lying down. In any case, the slides S2 are adjusted to the required alignment for height, and the slides S1 are adjusted to the required alignment for inter-pupillary distance, the guide-adjustment-lock means X then being tightened with the nuts 31. It is to be understood that the alignment is on a gravitational axis as may be required to deposit medication upon a specified target of the eye.

Having described only a typical preferred form and application of my invention, I do not wish to be limited or restricted to the specific details herein set forth, but wish to reserve to myself any modifications or variations that may appear to those skilled in the art as set forth within the limits of the following claims:

I claim:

1. A therapeutic frame for administering liquids by gravity from a dropper therefor to selective target areas of a person's eye, and including; a frame comprised of a nose bridge carrying spaced rims for disposition over each eye of the person, each of said rims having two right angularly spaced and parallel pairs of rails, two interfacially engaged slides carried over each of said right angularly spaced pairs of rails respectively and each having a transverse slot and one normally related to the other, and a guide-adjustment-lock means engaged through each of the two interfacially engaged slides to guide the dropper after adjustment of the slides for alignment with a target area of the person's eye and locked thereat to stop further movement of the slides.

2. The therapeutic frame for administering liquids to the eye as set forth in claim 1, wherein the two interfacially engaged slides are transparent for sight therethrough.

3. The therapeutic frame for administering liquids to the eye as set forth in claim 1, wherein the guide-adjustment-lock means is made of transparent material for translucency.

4. The therapeutic frame for administering liquids to the eye as set forth in claim 1, wherein the interfacially engaged slides slideably engage the parallel rails of the rims by opposed channel means hooked thereover.

5. The therapeutic frame for administering liquids to the eye as set forth in claim 1, wherein the interfacially engaged slides slideably engage over the opposite and parallel rails of the rims by opposed channel means.

6. The therapeutic frame for administering liquids to the eye as set forth in claim 1, wherein the guide-adjustment-lock means comprises a tubular barrel extending freely through the normally related slots, passing the dropper for alignment therewith.

7. The therapeutic frame for administering liquids to the eye as set forth in claim 1, wherein the guide-adjustment-lock means comprises a shouldered barrel engaged with one slide and a nut threaded thereon to engage with the other slide, the barrel having a bore passing the dropper for alignment therewith.

8. The therapeutic frame for administering liquids to the eye as set forth in claim 1, wherein the guide-adjustment-lock means comprises a tubular barrel with a tapered bore to receive a tapered dropper for stopped engagement therein and for alignment.

9. The therapeutic frame for administering liquids to the eye as set forth in claim 1, wherein the guide-adjustment-lock means comprises a shouldered barrel engaged with one slide and a nut threaded thereon to engage with the other slide, the barrel having a tapered bore to receive a tapered dropper for stopped engagement therein and for alignment.

10. The therapeutic frame for administering liquids to the eye as set forth in claim 1, wherein the two interfacially engaged slides are transparent for sight therethrough, and wherein the guide-adjustment-lock means comprises a tubular barrel extending freely through the normally related slots, passing the dropper for alignment therewith.

11. The therapeutic frame for administering liquids to the eye as set forth in claim 1, wherein the two interfacially engaged slides are transparent for sight therethrough, and wherein the guide-adjustment-lock means comprises a shouldered barrel engaged with one slide and a nut threaded thereon to engage with the other slide, the barrel having a bore passing the dropper for alignment therewith.

12. The therapeutic frame for administering liquids to the eye as set forth in claim 1, wherein the two interfacially engaged slides are transparent for sight therethrough, and wherein the guide-adjustment-lock means comprises a tubular barrel with a tapered bore to receive a tapered dropper for stopped engagement therein and for alignment.

13. The therapeutic frame for administering liquids to the eye as set forth in claim 1, wherein the two interfacially engaged slides are transparent for sight therethrough, and wherein the guide-adjustment-lock means comprises a shouldered barrel engaged with one slide and a nut threaded thereon to engage with the other slide, the barrel having a tapered bore to receive a tapered dropper for stopped engagement therein and for alignment.

* * * * *